United States Patent [19]

Elger et al.

[11] Patent Number: 4,626,531

[45] Date of Patent: Dec. 2, 1986

[54] PROSTAGLANDINS AND ANTIGESTAGENS FOR INDUCTION OF LABOR AND FOR ABORTION

[75] Inventors: Walter Elger; Sybille Beier, both of Berlin, Fed. Rep. of Germany

[73] Assignee: Schering Aktiengesellschaft, Berlin and Bergkamen, Fed. Rep. of Germany

[21] Appl. No.: 660,358

[22] Filed: Oct. 12, 1984

[30] Foreign Application Priority Data

Oct. 12, 1983 [DE] Fed. Rep. of Germany ....... 3337450

[51] Int. Cl.$^4$ .............................................. A61K 31/56
[52] U.S. Cl. ..................................................... 514/171
[58] Field of Search ......................................... 514/171

[56] References Cited

U.S. PATENT DOCUMENTS

| | | | |
|---|---|---|---|
| 4,094,977 | 6/1978 | Seeger et al. | 424/240 |
| 4,198,405 | 4/1980 | Enomoto et al. | 424/240 |
| 4,318,908 | 3/1982 | Enomoto et al. | 260/397.4 |
| 4,447,424 | 5/1984 | Teutsch et al. | 424/240 |

Primary Examiner—Elbert L. Roberts
Attorney, Agent, or Firm—Millen & White

[57] ABSTRACT

A pharmaceutical composition containing a prostaglandin and an antigestagen is suitable for induction of labor and for abortion.

31 Claims, 5 Drawing Figures

11β-(4-N,N-Dimethylaminophenyl)-17β-hydroxy-17α-propinyl-4,9(10)-estradien-3-on (RU-486)

11β-(4-Dimethylaminophenyl)-17α-hydroxy-17β-(3-hydroxypropyl)-13α-methyl-4,9-gonadien-3-on

CONTROLS

RU-486 +S

11β-(4-Dimethylaminophenyl)-17α-hydroxy-17β-
-(3-hydroxypropyl)-13α-methyl-4,9-gonadien-3-on    +S

FIG. 4-2

SULPROSTONE

PROSTAGLANDINS AND ANTIGESTAGENS FOR INDUCTION OF LABOR AND FOR ABORTION

BACKGROUND OF THE INVENTION

This invention relates to a combination product for combined use in the induction of labor or for abortion.

To avert danger for the mother and/or child, it is sometimes necessary to induce labor artificially or to terminate a pregnancy before term. Surgical techniques and pharmacological methods are available for this purpose.

A favorable pharmacological method is vaginal or intramuscular application of prostaglandins which, in the case of abortion, are taken in the first or second three-month period of pregnancy (Contraception 1983, Vol. 27, 51–60 and Int. J. Gynaecol. Obstet. 1982, Vol. 20, 383–386. Advantages of prostaglandins include their simple administrability and their applicability for use over a long period of pregnancy. Disadvantages include acute side effects such as pain and nausea; moreover, the success rate in the case of abortion in advanced phases of pregnancy is not over 90% even with a long period of prostaglandin treatment.

Another possibility of terminating a pregnancy consists in the application of an antigestagen (Med. et Hyg. 1982, Vol 40, 2087–2093). Antigestagens are better tolerated than prostaglandins but have a greater latency and individual variability of onset of action in comparison with prostaglandins.

SUMMARY OF THE INVENTION

Accordingly, it is an object of this invention to provide a new composition and method for induction of labor or abortion, which significantly ameliorates these problems.

Upon further study of the specification and appended claims, further objects and advantages of this invention will become apparent to those skilled in the art.

These objects have been attained based in part on this finding, that the PG type and AG type disadvantages are avoided or significantly ameliorated if prostaglandins (PG) and antigestagens (AG) are used together for these purposes.

BRIEF DESCRIPTION OF THE DRAWINGS

Various other objects, features and attendant advantages of the present invention will be more fully appreciated as the same becomes better understood when considered in conjunction with the accompanying drawings wherein:

FIGS. 3 and 4 show the results of an evaluation of synergistic antigestagen (AG)/Sulprostone(S) actions in advanced pregnancy in rats. Antigestagen: 3.0 mg/d s.c. days 13–15 p.c., Sulprostone: 0.1 mg 2×day 15 p.c., autopsy day 17 p.c.

DETAILED DISCUSSION

Surprisingly, the amounts by weight of prostaglandin and antigestagen can be greatly reduced in combined use in comparison with the usual amounts employed when they are used alone. Further surprising is the fact that the success rate of abortions or labor induction can even be increased as a result. The prostaglandin and antigestagen are advantageously used separately, simultaneously and/or sequentially. The weight ratio of prostaglandin to antigestagen is generally 1:20 to 1:6000, preferably 1:100 to 1:500.

These weight ratios are based on appropriate values for the two preferred active ingredients, i.e., sulprostone as the prostaglandin and 11$\beta$-[(4-N,N-dimethylamino)-phenyl]-17$\beta$-hydroxy-17$\alpha$-propinyl-4,9(10)-estradiene-3-one as the antigestagen. Corresponding weight ratios for any other ingredients can be readily determined using fully conventional techniques, e.g., involving differential potency studies using conventional protocols.

Prostaglandins suitable for use according to the invention are all prostaglandins suitable for abortion or inducing labor. These are well known. They particularly include prostaglandins of the E and F types. There can be mentioned for example: prostaglandin $E_2$, prostaglandin $F_{2\alpha}$, prostaglandin E derivatives, e.g., 16-phenoxy-$\omega$-17,18,19,20-tetranor-PGE$_2$-methylsulfonylamide (sulprostone), 16,16-dimethyl-trans-$\Delta$ $^2$-PGE$_1$-methyl ester (Gemeprost), 9-deoxo-16,16-dimethyl-9-methylene-PGE$_2$ (Metenenprost), prostaglandin F derivatives, e.g. 15-methyl-PGF$_{2\alpha}$-methyl ester, (5Z,13E)-(9R,11R,15R)-9-chloro-11,15-dihydroxy-16,16-dimethyl-5,13-prostadienoic acid (DE-OS No. 29 50 027), (5Z,13E)-(9R,11R,15R)-11,15-dihydroxy-9-fluoro-16-phenoxy-17,18,19,20-tetranor-5,13-prostadienoic acid (DE-OS No. 31 26 924), (5Z,13E)-(9R,11R,15R)-11,15-dihydroxy-16,16-dimethyl-9-fluoro-5,13-prostadienoic acid (DE-OS No. 31 26 924), (5Z,13E)-(9R,11R,15R)-9-bromo-11,15-dihydroxy-16-phenoxy-17,18,19,20-tetranor-5,13-prostadienoic acid (DE-OS No. 31 48 743), or (5Z,13E)-(9R,11R,15R)-9-bromo-11,15-dihydroxy-16,16-dimethyl-5,13-prostadienoic acid (DE-OS 31 48 743), etc.

This listing is exemplary only. Many other prostaglandins can be used.

The prostaglandins can be used in amounts that are clearly lower than the generally normal amounts for abortion or induction of labor. The amount to be used according to the invention conventionally depends, inter alia, on the hormone level, the period of the pregnancy, etc., of the patient and the manner of application. Precise dosages can be routinely determined using conventional techniques in view of this disclosure. When sulprostone is used as the prostaglandin, as a rule 0.03 to 0.5 mg per day suffices. Application can, for example, be made locally, topically, enterally or parenterally. Upon intramuscular injection or intravenous infusion, for example, amounts of about 0.1 to 0.3 mg of sulprostone per day are satisfactory. Upon local application, for example extra-amniotically or intravaginally, about 0.03 to 0.5 mg of sulprostone per day is used. For topical application, transdermal systems, such as skin plasters, can be used. According to this invention, biologically equivalent amounts of other prostaglandins can be used instead of sulprostone. These bioavailability equivalent amounts can be determined routinely and conventionally, e.g., by performing differential potency studies using fully routine pharmacological protocols, e.g., W. Elger, Animal Reproduction Science 2 (1979), 133.

The combined treatment with prostaglandin and antigestagen occurs as a rule over 1 to 4, preferably 1 to 2 days, during which time the prostaglandin and antigestagen can be applied preferably separately and simultaneously, or also separately and sequentially. The prostaglandin and antigestagen can also be combined in a single dosage unit. In sequential therapy, preferably, first the antigestagen is applied for 1 to 4 days and then the prostaglandin alone, or the prostaglandin and additional antigestagen together, over 24 hours. The application of the antigestagen for 1 or for 4 days depends on the period of pregnancy and on the progesterone level.

All compounds are suitable as antigestagens for this invention which have a strong affinity for the gestagen receptor (progesterone receptor) and yet show no progestational activity of their own, thus functioning as antigestagens. For example, the following steroids are suitable as such competitive progesterone antagonists:

11β-[(4-N,N-dimethylamino)-phenyl]-17β-hydroxy-17α-propinyl-4,9(10)-estradien-3-one, 11β-[(4-N,N-dimethylamino)-phenyl]-17β-hydroxy-18-methyl-17α-propinyl-4,9(10)-estradien-3-one, 11β-[4-N,N-dimethylamino)-phenyl]-17aβ-hydroxy-17aα-propinyl-D-homo-4,9(10),16-estratrien-3-one, (European patent application No. 82400025.1—Publication No. 0 057 115);

11β-p-methoxyphenyl-17β-hydroxy-17α-ethinyl-4,9(10)-estradien-3-one (Steroids 37 (1981) 361–382), or 11β-(4-dimethylaminophenyl)-17α-hydroxy-17β-(3-hydroxypropyl)-13α-methyl-4,9-gonadien-3-one.

Also suitable for use in this invention are antigestagens which antagonize the effect of gestagens per se, i.e., operate by a route different from competing with the gestagen receptor. Suitable such antigestagens include the derivatives of trilostane (U.S. Pat. No. 4,160,027).

The foregoing listing is exemplary only. Many other antigestagens can be used, e.g., as disclosed in Fertility and Sterility 40, 253 (1982), Steroids 37, 361 (1981).

The antigestagens according to this invention are used in amounts that as a rule are also lower than the generally normal amounts for abortion or labor induction. In general, 10–200 mg of 11β-[(4-N,N-dimethylamino)-phenyl]-17β-hydroxy-17α-propinyl-4,9(10)-estradien-3-one per day or a biologically equivalent amount of another antigestagen suffice. Precise dosages can be routinely determined using conventional techniques in view of this disclosure. The mentioned bioequivalent amounts can be determined conventionally and routinely, e.g., by performing differential potency studies using fully routine pharmacological protocols, e.g., Fertility and Sterility 40, 253 (1982), Steroids 37, 361 (1981).

The antigestagens can, for example, be applied locally, topically, enterally or parenterally.

For the preferred oral application of either component, tablets, coated tablets, capsules, pills, suspensions or solutions are suitable. These can be produced in the usual way using the admixtures and vehicles customary in galenicals, most notably those well known for formulations of PG and AG compounds. For local or topical application, for example, vaginal suppositories or transdermal systems such as skin plasters are suitable.

A dosage unit generally contains about 10 to 200 mg of antigestagen. Suitable hosts are mammals including humans. Other than as indicated herein, administration will be analogous to that of the known active ingredients alone.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

Composition of a freeze-dried sulprostone formulation per ampoule

| | |
|---|---|
| 0.1 mg | Sulprostone |
| 5.0 mg | Polyvinylpyrrolidone (K value = 15–18) |
| 1.95 mg | Tris(hydroxymethyl)aminomethane hydrochloride (tremetamol.HCl) (from 1.5 mg tremetamol and 1N hydrochloric acid) |
| 7.05 mg | |

For dosage and application, the content of the ampoule is dissolved with isotonic saline solution for intramuscular injection or intravenous infusion for extraamniotic application.

Production of the dry substance

Sulprostone is brought to solution by addition to an ice-cooled solution of polyvinylpyrrolidone and tremetamol in distilled water. The pH of the solution is adjusted to 5.0 by addition of 1N hydrochloric acid with strong cooling. Then the solution was filled to the required volume. After filtering with a membrane filter, the solution is dosed in ampoules.

The solution is then frozen by immersion of the ampoules in an acetone/dry ice freezing mixture and immediately freeze-dried in a precooled freeze-dry unit for about 48 hours. After completion of the freeze-drying, the ampoules are immediately sealed.

EXAMPLE 2

Composition of a film with sulprostone for vaginal application

| | |
|---|---|
| 0.1 mg | Sulprostone |
| 19.6 mg | Hydroxypropyl cellulose |
| 0.32 mg | Polyoxyethylenepolyoxypropylene polymer (Pluronic F 68 ®) |
| 20.02 mg | |

The film has a length of 3 cm.

EXAMPLE 3

Composition of a film with sulprostone for buccal application

| | |
|---|---|
| 0.3 mg | Sulprostone |
| 9.16 mg | Hydroxypropyl cellulose |
| 9.16 mg | Cellulose fibers |
| 0.15 mg | Polyoxyethylenepolyoxypropylene polymer (Pluronic F 68 ®) |
| 18.77 mg | |

The surface of the film is 1.2×1.2 cm.

EXAMPLE 4

Composition of a tablet with sulprostone for vaginal application

| | |
|---|---|
| 0.1 mg | Sulprostone |
| 238.9 mg | Lactose |
| 110.0 mg | microcrystalline cellulose |
| 1.0 mg | Magnesium stearate |
| 350.0 mg | |

EXAMPLE 5

Composition of another tablet with 11β-[(4-N,N-Dimethylamino)-phenyl]-17β-hydroxy-17α-propinyl-4,9(10)-estradien-3-one for oral application

| | |
|---|---|
| 10.0 mg | 11β-[(4-N,N—Dimethylamino)-phenyl]-17β-hydroxy-17α-propinyl-4,9(10)-estradien-3-one |
| 140.5 mg | Lactose |
| 69.5 mg | Corn starch |
| 2.5 mg | Polyvinylpyrrolidone 25 |
| 2.0 mg | Aerosil |
| 0.5 mg | Magnesium stearate |
| 225.0 mg | Total weight |

Pharmacological observations

The prostaglandin sulprostone and the antigestagens 11β-[(4-N,N-dimethylamino)-phenyl]-17β-hydroxy-17α-propinyl-4,9(10)-estradien-3-one (RU 38486) and 11β-(4-dimethylaminophenyl)-17α-hydroxy-17β-(3-hydroxypropyl)-13α-methyl-4,9-gonadien-3-one were selected as model substances for a pilot test on pregnant guinea pigs and rats. The dosages tested can be gathered from Table 1 and FIGS. 1 to 4.

(1) Research on pregnant guinea pigs (1.1) Testing of the combination

Description of the test

Pregnant guinea pigs with a body weight of about 800 g were taken on the 42nd day of pregnancy for the test (the second day of the vaginal opening in the mating season was counted as the first day of pregnancy). Pregnancy was checked by palpation before beginning of the test. The treatment took place with the selected test substances or the combination by daily injection on the 43rd and 44th day of pregnancy. For this purpose, the test substances were dissolved in benzyl benzoate+castor oil (ratio of the mixture in the case of sulprostone: 1+2; RU 38486: 2+4.5) and the daily dose was injected s.c. in a volume of 0.4 ml (sulprostone) or of 1.0 ml (RU 38486). The possible expulsion of the fetus was checked during and after treatment several times daily. On the 50th day of pregnancy, the animals were sacrificed. The uteri were examined and the fetuses found.

Results:

The results of the tests for induction of abortion in pregnant guinea pigs with combined administration of antigestagen and prostaglandin are summarized in Table 1.

TABLE 1

Comparative examination of the abortive action of sulprostone (PG), RU-38.486 (competitive progesterone antagonist) and the combination of both substances in pregnant guinea pigs.) Treatment d43 and d44, autopsy on d50.

| Dose mg/d s.c. | n animals with abort./ n total animals | | S-/RU - combination |
|---|---|---|---|
| | Sulpro- tone(S) | RU-38.486 | |
| 30.0 | — | 4/9 | 0.03 mg Sulprostone ⎫ |
| 10.0 | — | 3/9 | + ⎬ 7/9 |
| 3.0 | — | 1/8 | 10.0 mg RU-38.486 ⎭ |
| 1.0 | — | | 0.03 mg Sulprostone ⎫ |
| 0.3 | 10/10 | | + ⎬ 4/8 |
| 0.1 | 8/10 (2/10)* | | 3.0 mg RU-38.486 ⎭ |
| 0.03 | 3/10 | | |
| 0.01 | 0/9 | | |

( )* = 'missed abortions'

Sulprostone:

The abortifacient action of sulprostone was dependent on dosage. An abortion rate of 30% (=abortion in 3 out of 10 animals treated) was found in the case of a dose of 0.03 mg/d s.c. Expulsion of the embryos from the uterus occurred with this dose with a latency of about 1-2 days (see FIG. 1).

Antigestagens:

With antigestagen RU 38486 a termination of an existing pregnancy with 30 mg/d s.c. was to be obtained in 4 out of 9 animals treated. With a dose of 10.0 mg/d the abortion rate was 3/9 animals treated. After 3.0 mg/d s.c. only 1 out of 8 animals treated aborted. The abortions occurred with latency of 4 to 7 days from the beginning of treatment (see FIG. 1).

AG/PG combination:

The combination of subabortive antigestagen doses (3.0 mg or 10.0 mg RU 38486/d s.c.) with a marginally effective sulprostone dose of 0.03 mg/d s.c. led, in comparison with only antigestagen treatment, in each case to a clearly higher abortion rate and to a far faster induction of abortions. The interval of induction of abortion was also shorter than with only PG treatment, to the extent that the latter caused expulsion of the primordium at all (see table 1 and FIG. 1).

1.2 Testing with sequential treatment

Description of the test

Pregnant guinea pigs with a body weight of about 800 g were taken on the 42nd day of pregnancy for the tests (the second day of the vaginal opening in the mating season was counted as the first day of pregnancy). Pregnancy was checked by palpation before beginning of the test. The treatment took place with the selected antigestagens by daily injection on the 43rd and 44th day of pregnancy. The prostaglandin was applied on the 45th day. For this purpose the antigestagen was dissolved in benzyl benzoate+castor oil (mixture ratio 2+4.5) and the daily dose injected subcutaneously in a volume of 1.0 ml. The sulprostone was put in the galenical preparation of the Nalador ® ampoule and injected subcutaneously. The possible expulsion of fetuses was checked during and after treatment several times daily. On the 50th day of pregnancy the animals were sacrificed. The uteri were inspected and the fetuses found.

Figure 1:
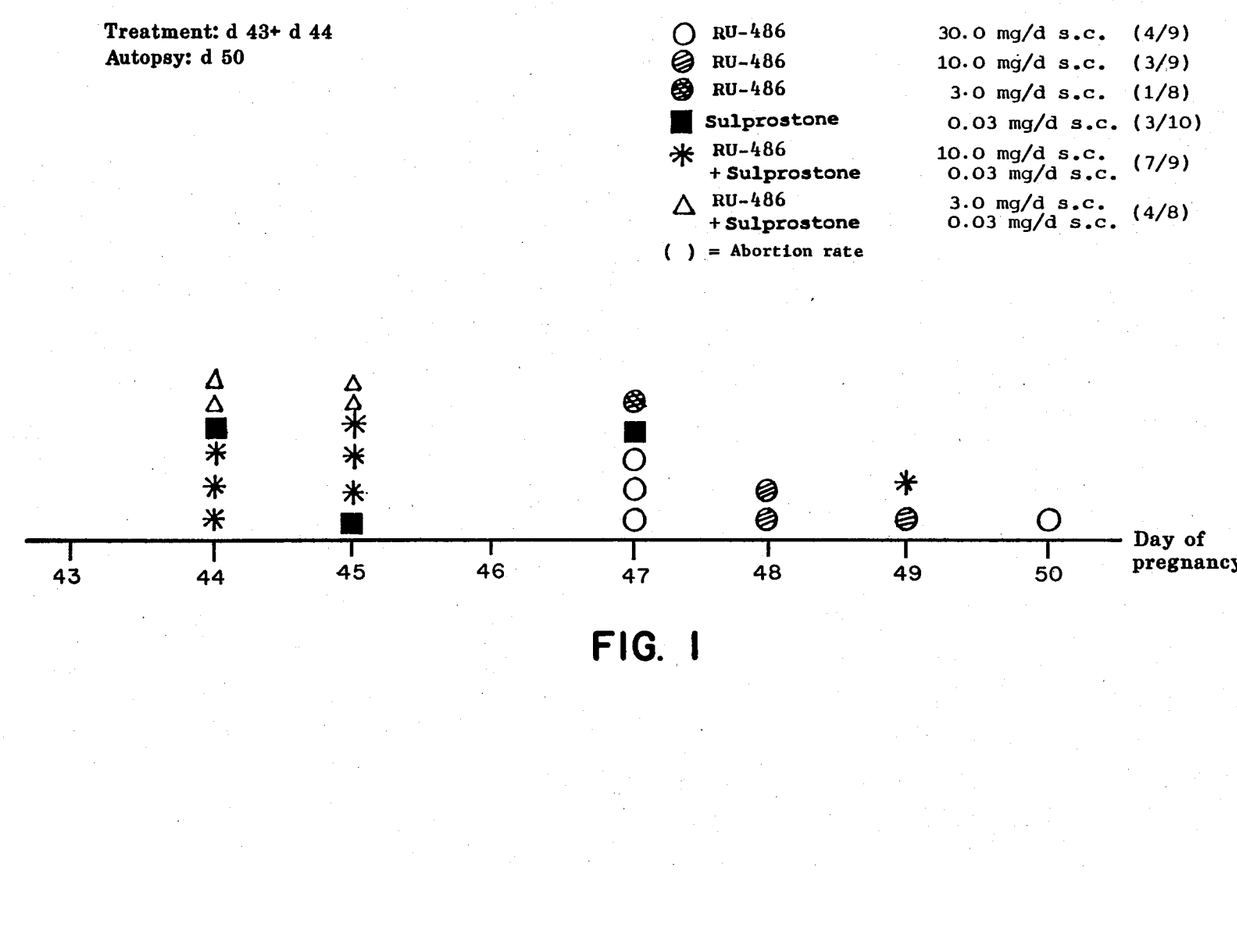
FIG. 1 illustrates the results of tests involving the termination of pregnancy in guinea pigs. The day of abortion is shown under various treatment conditions.
Figure 2:
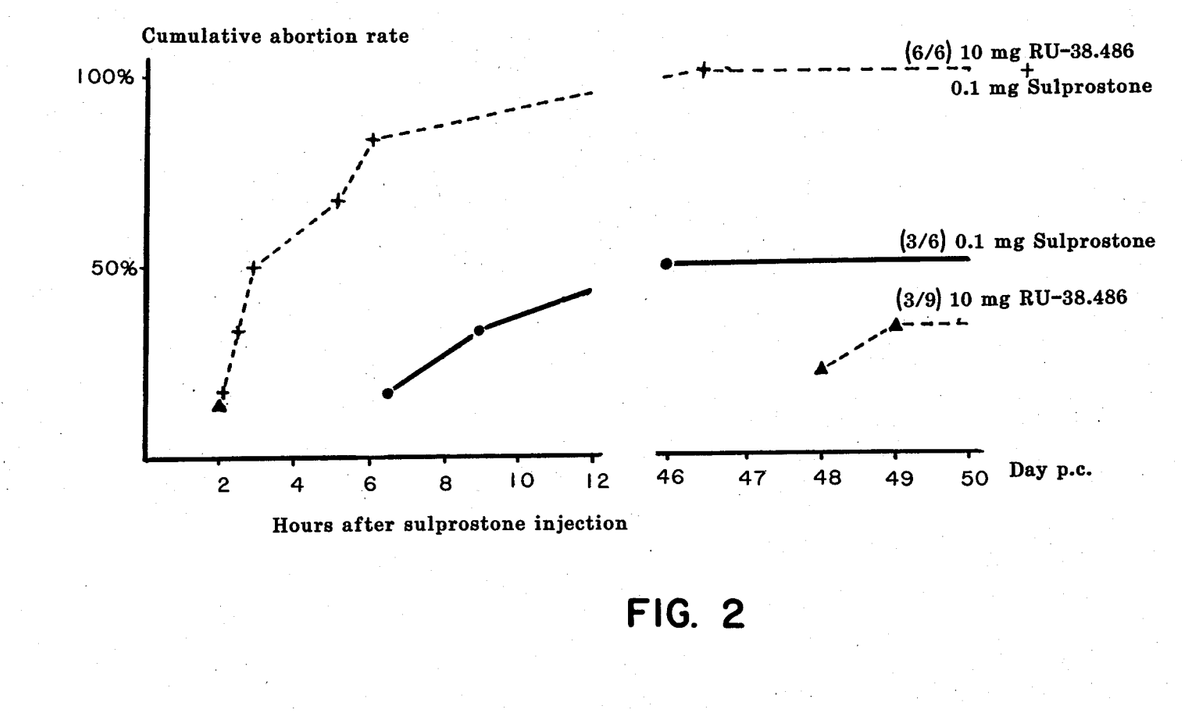
FIG. 2 shows the results of a comparative test of the abortive action of sulprostone (PG) and RU-38.486 (AG) and the sequential use of both substances in pregnant guinea pigs (s.c. administration)

Results:

The results of the tests for induction of abortion in pregnant guinea pigs in sequential application of antigestagen and prostaglandins are summarized in FIG. 2.

Sulprostone:

With a dose of 0.1 mg sulprostone/d s.c. an abortion rate of 50% (=abortion in 3 out of 6 animals treated) was found. Expulsion of embryos from the uterus occurred with this dose with a latency of about 6–24 hours (see FIG. 2).

Antigestagens:

With antigestagen RU 38486 a termination of an existing pregnancy with 10 mg/c s.c. in 3 out of 9 animals treated was achieved. However, the abortion occurred only on the 48th or 49th day, i.e., with a latency of 5 to 6 days from the beginning of treatment (see FIG. 2).

AG/PG sequential treatment:

With sequential administration of the above mentioned marginally effective AG and PG doses, termination of pregnancy in all guinea pigs (6/6 animals) occurred (see FIG. 2), in which the latency period was much shorter than with only PG treatment, to the extent that the latter was successful at all (median value: 4 hours versus 12 to 24 hours).

(2) Research on pregnant rats

Description of test

The tests were conducted on female Wistar rats of an in-house breed with a weight of about 200 g. After mating had occurred, the beginning of pregnancy was assured by determination of sperm in a vaginal smear.

The day of determination of sperm is considered as day 1 of pregnancy (=d1 p.c.).

The antigestagens were dissolved in a benzyl benzoate-castor oil mixture (ratio 1+4). The vehicle volume per individual dose was 0.2 ml. The treatment was subcutaneous.

Figure 3:
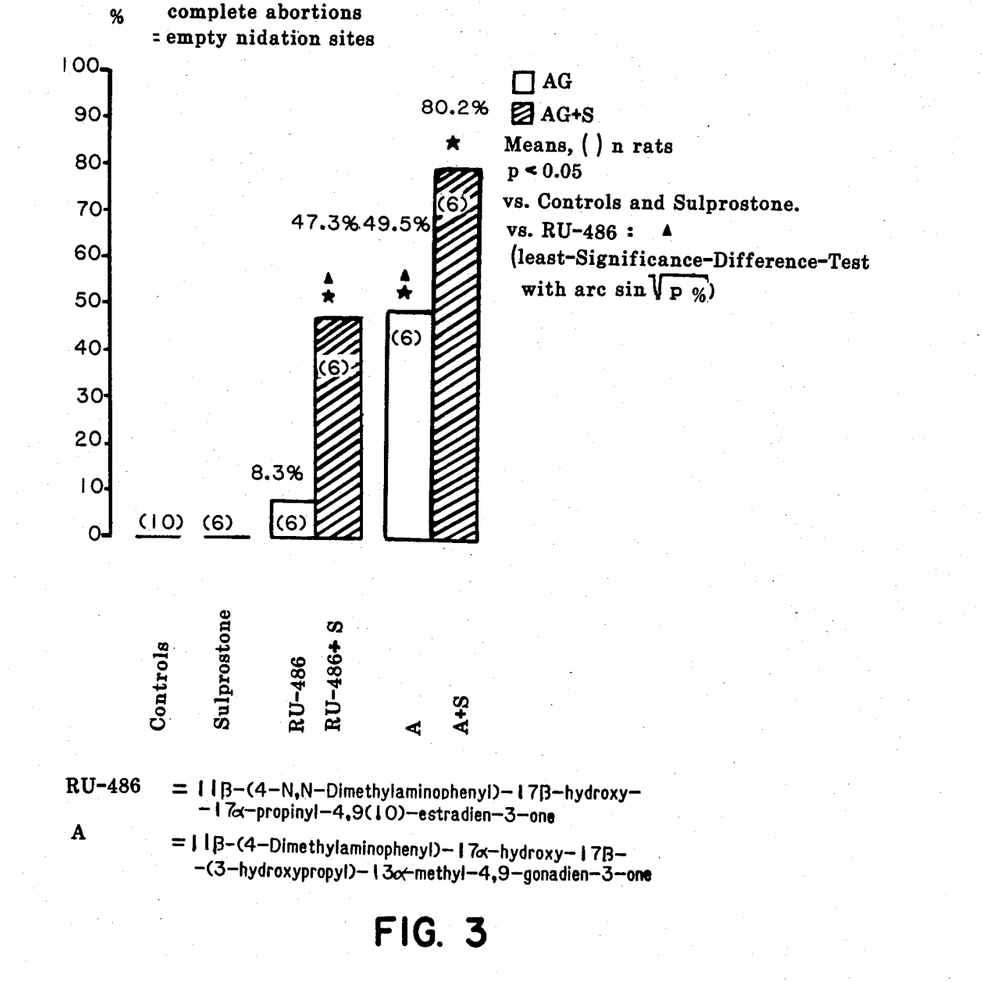

The dosages selected can be gathered from FIG. 3.

The prostaglandin sulprostone was dissolved in a mixture of ethanol+benzyl benzoate+castor oil (ratio 1+5+12). The vehicle volume of the selected individual dose of 0.1 mg was 0.2 ml. Sulprostone was applied subcutaneously.

Pregnancy was checked by palpation before beginning of the test. Assignment of the pregnant animals to the various test groups was done randomly (n=6/group). With administration only of the antigestagens selected, the treatment took place by injection from d13–d15 of pregnancy. Groups, which were given a combined antigestagen/prostaglandin treatment, received, in addition, 2×0.1 mg sulprostone/animal s.c. on d15 p.c.

Only sulprostone (2×0.1 mg/animal s.c. on d15 p.c.) was administered to another group. From d13–15 p.c. 0.2 ml of the benzyl benzoate-castor oil vehicle was applied daily to the control group. The rats were sacrificed on d17 p.c. and the uteri were examined for living and dead fetuses, retained placentas and empty nidation sites. The percentage of complete abortions (by definition: empty nidation site) was calculated per group.

Results:

The results of the tests for induction of abortion in pregnant rats are documented in FIGS. 3 and 4.

Treatment with effective antigestagens led to induction of abortions in rats. However, there is a tendency to incomplete abortions, in part, the abortions go along with prolonged, continuous vaginal bleeding. (A corresponding behavior was observed in the first clinical research with RU-486 at the time of suppressed menstruation.)

The percentage of complete abortions with 3-day s.c. administration of 3.0 mg/d s.c. was 49.5% for the test substance 11β-(4-dimethylaminophenyl)-17α-hydroxy-17β-(3-hydroxypropyl)-13α-methyl-4,9-gonadien-3-one. After administration of 3.0 mg of RU-486/d s.c., the rate of complete abortions was 8.3%. Additional sulprostone administration of 2×0.1 mg/d s.c. on day 15 could clearly increase the abortive effectiveness of 11β-(4-dimethylaminophenyl)-17α-hydroxy-17β-(3-hydroxypropyl)-13α-methyl-4,9-gonadien-3-one and RU-486 (see FIGS. 3 and 4).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising a labor or abortion inducing prostaglandin and a labor or abortion inducing antigestagen, the total amount of the combination of the prostaglandin and the antigestagen being effective to induce labor or an abortion.

2. A pharmaceutical composition of claim 1 wherein the amount of the prostaglandin and the amount of the antigestagen are both lower than the amount at which each is effective to induce labor or abortion when used alone.

3. A pharmaceutical composition of claim 1, wherein at least one of the amount of the prostaglandin and the amount of the antigestagen is lower than the amount at which it is effective to induce labor or abortion when used alone.

4. A pharmaceutical composition of claim 1, wherein the prostaglandin and antigestagen are contained in a weight ratio of 1:20 to 1:6000.

5. A pharmaceutical composition of claim 1, wherein the prostaglandin and the antigestagen are contained in separate dosage units.

6. A pharmaceutical composition of claim 1, wherein the prostaglandin and the antigestagen are contained in the same dosage unit.

7. A pharmaceutical composition of claim 1, wherein the prostaglandin is 0.03–0.5 mg of 16-phenoxy-ω-17,18,19,20-tetranor-PGE$_2$-methylsulfonylamide or a biologically equivalent amount of another prostaglandin.

8. A pharmaceutical composition of claim 1, wherein the antigestagen is 10–200 mg of 11β-[(4-N,N-dimethylaminophenyl]-17β-hydroxy-17α-propinyl-4,9(10)-estradien-3-one or a biologically equivalent amount of another antigestagen.

9. A pharmaceutical composition of claim 1, wherein the prostaglandin is prostaglandin E$_2$, prostaglandin F$_{2\alpha}$ 16-phenoxy-ω-17,18,19,20-tetranor-PGE$_2$-methylsulfonylamide, 16,16-dimethyl-trans-Δ$^2$-PGE$_1$-methyl ester, 9-deoxo-16,16-dimethyl-9-methylene-PGE$_2$, a prostaglandin F derivative, 15-methyl-PGF$_{2\alpha}$-methyl ester, (5Z,13E)-(9R,11R,15R)-9-chloro-11,15-dihydroxy-16,16-dimethyl-5,13-prostadienoic acid, (5Z,13E)-(9R,11R,15R)-11,15dihydroxy-9-fluoro-16-phenoxy-17,18,19,20-tetranor-5,13-prostadienoic acid, (5Z,13E)-(9R,11R,15R)-11,15-dihydroxy-16,16-dimethyl-9-fluoro-5,13-prostadienoic acid (DE-OS 31 26 924), (5Z,13E)-(9R,11R,15R)-9-bromo-11,15-dihydroxy-16-phenoxy-17,18,19,20-tetranor-5,13-prostadienoic acid, or (5Z,13E)-(9R,11R,15R)-9-bromo-11,15-dihydroxy-16,16-dimethyl-5,13-prostadienoic acid.

10. A pharmaceutical composition of claim 1, wherein the antigestagen is
11β-[(4-N,N-dimethylamino)-phenyl]-17β-hydroxy-17α-propinyl-4,9(10)-estradien-3-one,
11β-[(4-N,N-dimethylamino)-phenyl]-17β-hydroxy-18-methyl-17α-propinyl-4,9(10)-estradien-3-one,
11β-[4-N,N-dimethylamino)-phenyl]-17aβ-hydroxy-17a$_\alpha$-propinyl-D-homo-4,9(10),16-estratrien-3-one,
11β-p-methoxyphenyl-17β-hydroxy-17α-ethinyl-4,9(10)-estradien-3-one, or
11β-(4-dimethylaminophenyl)-17α-hydroxy-17β-(3-hydroxypropyl)-13α-methyl-4,9-gonadien-3-one.

11. A pharmaceutical composition of claim 7 wherein the prostaglandin is 0.1 to 0.3 mg of 16-phenoxy-ω-17,18,19,20-tetranor-PGE$_2$-methylsulfonylamide or a biologically equivalent amount of another prostaglandin and the composition is adapted for i.m. or i.v. administration.

12. A pharmaceutical composition of claim 7 wherein the prostaglandin is 0.03 to 0.5 mg of 16-phenoxy-ω-17,18,19,20-tetranor-PGE$_2$-methylsulfonylamide or a biologically equivalent amount of another prostaglandin and the composition is adapted for local administration.

13. A pharmaceutical composition of claim 4, wherein the amount of antigestagen is 10–200 mg per dosage unit of 11β-[(4-N,N-dimethylamino)-phenyl]-17β-hydroxy-17α-propinyl-4,9(10)-estradine-3-one or a biologically equivalent amount of another antigestagen.

14. A method of inducing an abortion in a pregnant patient comprising administering to the patient an effective amount of a composition of claim 1.

15. A method of inducing labor in a pregnant patient comprising administering to the patient an effective amount of a composition of claim 1.

16. A method of claim 14, wherein the administration of the prostaglandin and the antigestagen is simultaneous.

17. A method of claim 14, wherein the administration of the prostaglandin and the antigestagen is sequential.

18. A method of claim 14, wherein the prostaglandin and the antigestagen are administered in separate dosage units.

19. A method of claim 15, wherein the administration of the prostaglandin and the antigestagen is simultaneous.

20. A method of claim 15, wherein the administration of the prostaglandin and the antigestagen is sequential.

21. A method of claim 15, wherein the prostaglandin and the antigestagen are administered in separate dosage units.

22. A method of inducing an abortion in a pregnant patient comprising administering to the patient an effective amount of a composition of claim 3.

23. A method of inducing labor in a pregnant patient comprising administering to the patient an effective amount of a composition of claim 3.

24. A method of inducing an abortion in a pregnant patient comprising administering to the patient an effective amount of a composition of claim 7.

25. A method of inducing labor in a pregnant patient comprising administering to the patient an effective amount of a composition of claim 7.

26. A method of inducing an abortion in a pregnant patient comprising administering to the patient an effective amount of a composition of claim 8.

27. A method of inducing labor in a pregnant patient comprising administering to the patient an effective amount of a composition of claim 8.

28. A method of inducing an abortion in a pregnant patient comprising administering to the patient an effective amount of a composition of claim 9.

29. A method of inducing labor in a pregnant patient comprising administering to the patient an effective amount of a composition of claim 9.

30. A method of inducing an abortion in a pregnant patient comprising administering to the patient an effective amount of a composition of claim 10.

31. A method of inducing labor in a pregnant patient comprising administering to the patient an effective amount of a composition of claim 10.

* * * * *